US00PP29084P3

(12) United States Plant Patent
Nebelmeir

(10) Patent No.: US PP29,084 P3
(45) Date of Patent: Mar. 6, 2018

(54) ***PORTULACA* PLANT NAMED 'LAZPRT1507'**

(50) Latin Name: ***Portulaca umbraticola* Kunth**
Varietal Denomination: LAZPRT1507

(71) Applicant: Johannes Sebastian Nebelmeir, Marling (IT)

(72) Inventor: Johannes Sebastian Nebelmeir, Marling (IT)

(73) Assignee: Lazzari Societa Agricola a R. L., Sabaudia (IT)

( * ) Notice: Subject to any disclaimer, the term of this patent is extended or adjusted under 35 U.S.C. 154(b) by 53 days.

(21) Appl. No.: 14/999,371

(22) Filed: Apr. 30, 2016

(65) Prior Publication Data

US 2017/0318725 P1 Nov. 2, 2017

(51) Int. Cl.
*A01H 5/02* (2006.01)

(52) U.S. Cl.
USPC ..... Plt./471

(58) Field of Classification Search
USPC ..... Plt./471
See application file for complete search history.

(56) References Cited

PUBLICATIONS

UPOV-PLUTO:Plant Variety Database—Aug. 4, 2017, citation for cultivar name, 'LAZPRT1507' (1 page total).*

* cited by examiner

*Primary Examiner* — Susan McCormick Ewoldt
(74) *Attorney, Agent, or Firm* — C. A. Whealy

(57) ABSTRACT

A new and distinct cultivar of *Portulaca* plant named 'LAZPRT1507', characterized by its semi-upright to spreading growth habit; vigorous growth habit; freely branching habit; freely flowering habit; fully double intense red-colored flowers; and excellent garden performance.

1 Drawing Sheet

Botanical designation: *Portulaca umbraticola* Kunth.
Cultivar denomination: 'LAZPRT1507'.

CROSS-REFERENCED TO CLOSELY-RELATED APPLICATIONS

Title: *Portulaca* Plant Named 'LAZPRT1508'
Applicant: Johannes Sebastian Nebelmeir
Filed: Concurrently with the instant application

BACKGROUND OF THE INVENTION

The present invention relates to a new and distinct cultivar of *Portulaca* plant, botanically known as *Portulaca umbraticola* Kunth, commonly known as Wingpod Purslane, and hereinafter referred to by the name 'LAZPRT1507'.

The new *Portulaca* plant is a product of a planned breeding program conducted by the Inventor in Merano, South Tyrol, Italy. The objective of the breeding program is to create new vigorous and freely branching *Portulaca* plants with numerous fully double flowers.

The new *Portulaca* plant is a naturally-occurring whole plant mutation of a proprietary selection of *Portulaca umbraticola* Kunth identified as code number III/11-A, not patented. The new *Portulaca* plant was discovered and selected by the Inventor as a flowering plant from within a population of plants of the parent selection in a controlled greenhouse environment in Merano, South Tyrol, Italy during the spring of 2014.

Asexual reproduction of the new *Portulaca* plant cuttings in a controlled greenhouse environment in Merano, South Tyrol, Italy since the spring of 2014, has shown that the unique features of this new *Portulaca* plant are stable and reproduced true to type in successive generations.

SUMMARY OF THE INVENTION

Plants of the new *Portulaca* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LAZPRT1507'. These characteristics in combination distinguish 'LAZPRT1507' as a new and distinct *Portulaca* plant:

1. Semi-upright to spreading growth habit.
2. Vigorous growth habit.
3. Freely branching habit.
4. Freely flowering habit.
5. Fully double intense red-colored flowers.
6. Excellent garden performance.

Plants of the new *Portulaca* can be compared to plants of the parent selection. Plants of the new *Portulaca* differ primarily from plants of the parent selection in flower color as plants of the parent selection have orange red-colored flowers.

Plants of the new *Portulaca* can also be compared to plants of *Portulaca umbraticola* Kunth 'LAZPRT1508', disclosed in a U.S. Plant Patent application filed concurrently. Plants of the new *Portulaca* differ primarily from plants of 'LAZPRT1508' in flower color as plants of 'LAZPRT1508' have red purple-colored flowers.

Plants of the new *Portulaca* can be compared to plants of *Portulaca oleracea* 'Dynamite Lemon Yellow', not patented. In side-by-side comparisons, plants of the new *Portulaca* differ primarily from plants of 'Dynamite Lemon Yellow' in the following characteristics:

1. Flowers of plants of the new *Portulaca* are more fully double with more petaloids per flower than flowers of plants of 'Dynamite Lemon Yellow'.
2. Plants of the new *Portulaca* and 'Dynamite Lemon Yellow' differ in petal and petaloid color as plants of 'Dynamite Lemon Yellow' have lemon yellow-colored petals and petaloids.

BRIEF DESCRIPTION OF THE PHOTOGRAPH

The accompanying colored photograph illustrates the overall appearance of the new *Portulaca* plant showing the colors as true as it is reasonably possible to obtain in colored reproductions of this type. Colors in the photograph may differ slightly from the color values cited in the detailed botanical description which accurately describe the colors of the new *Portulaca* plant.

The photograph comprises a side perspective view of a typical flowering plant of 'LAZPRT1507' grown in an outdoor nursery.

DETAILED BOTANICAL DESCRIPTION

The aforementioned photograph and following observations, measurements and values describe plants grown during the summer in an outdoor nursery in Merano, South Tyrol, Italy and under cultural practices typical of commercial *Portulaca* production. During the production of the plants, day and night temperatures ranged from 13.8° C. to 28.6° C. and light levels ranged from 60 to 70 klux. Plants were four months old when the photograph and the description were taken. In the description, color references are made to The Royal Horticultural Society Colour Chart, 1995 Edition, except where general terms of ordinary dictionary significance are used.

Botanical classification: *Portulaca umbraticola* Kunth 'LAZPRT1507'.

Parentage: Naturally-occurring whole plant mutation of a proprietary selection of *Portulaca umbraticola* Kunth identified as code number III/11-A, not patented.

Propagation:

*Type*.—By cuttings.

*Time to initiate roots, summer*.—About 10 days at temperatures about 22° C.

*Time to initiate roots, winter*.—About 14 days at temperatures about 22° C.

*Time to produce a rooted young plant, summer*.—About 24 days at temperatures about 22° C.

*Time to produce a rooted young plant, winter*.—About 28 days at temperatures about 15° C.

*Root description*.—Fine, fibrous.

*Rooting habit*.—Freely branching; medium density.

Plant description:

*Plant and growth habit*.—Semi-upright to spreading plant habit; vigorous growth habit; relatively rapid growth rate.

*Branching habit*.—Freely branching habit with lateral branches developing at every node; pinching is not required.

*Overall plant height*.—About 15 cm.

*Plant diameter* (*area of spread*).—About 42 cm.

Lateral branch description:

*Length*.—About 30 cm to 55 cm.

*Diameter*.—About 5 mm.

*Internode length*.—About 3 mm to 30 mm.

*Strength*.—Moderately strong.

*Texture*.—Smooth, glabrous; succulent.

*Color*.—Close to 148A underlain with close to 177A and 185B.

Leaf description:

*Arrangement*.—Opposite, subtending the flowers, whorled; simple.

*Length*.—About 1.8 cm to 4 cm.

*Width*.—About 7 mm to 15 mm.

*Shape*.—Obovate.

*Apex*.—Initially acute becoming more rounded with development.

*Base*.—Obtuse.

*Margin*.—Entire.

*Texture, upper and lower surfaces*.—Smooth, glabrous; succulent.

*Venation pattern*.—Pinnate.

*Color*.—Developing leaves, upper surface: Close to 137A. Developing leaves, lower surface: Close to 147C. Fully expanded leaves, upper surface: Close to 146A; when exposed to full sunlight, margins become closer to 185B in color; venation, close to 147B. Fully expanded leaves, lower surface: Close to 148B; venation, close to 147B.

*Petioles*.—Length: About 2 mm. Diameter: About 2 mm. Texture, upper and lower surfaces: Smooth, glabrous; succulent. Color, upper and lower surfaces: Close to 146C.

Flower description:

*Flowering habit and arrangement*.—Fully double rotate flowers clustered in terminal cymes; freely flowering habit with potentially about 20 to 50 flowers developing per inflorescence during the flowering season; flowers face mostly upright; flowers remain open during the day and early evening and do not close until late at night.

*Fragrance*.—None detected.

*Natural flowering season*.—Plants begin flowering about six to eight weeks after planting; in the garden, plants flower recurrently from mid-spring to mid-autumn in Italy.

*Flower longevity*.—Flowers last about three days on the plant; flowers not persistent.

*Inflorescence diameter*.—About 5 cm.

*Inflorescence height*.—About 2 cm.

*Flower diameter*.—About 3.2 cm.

*Flower length* (*height*).—About 1.4 cm.

*Flower buds*.—Length: About 1 cm. Diameter: About 5 mm. Shape: Ovoid. Color: Close to 147B.

*Petals*.—Quantity and arrangement: Five petals in a single whorl. Length: About 1.6 cm. Width: About 1 cm. Shape: Obovate. Apex: Emarginate. Base: Truncate. Margin: Entire. Texture, upper and lower surfaces: Smooth, glabrous. Color: When opening, upper surface: Close to 43A. When opening, lower surface: Close to 33A. Fully opened, upper surface: Close to 43A marbled with close to 33A; after anthesis, color becomes closer to 53B. Fully opened, lower surface: Close to 33B shifting to closer to 17B; after anthesis, color becomes closer to 53B.

*Petaloids*.—Quantity and arrangement: About 100 clustered at the center of the flower. Length: About 1.2 cm. Width: About 2.5 mm, variable. Shape: Oblanceolate. Apex: Acute to acuminate, variable. Base: Attenuate. Margin: Entire. Texture, upper and lower surfaces: Smooth, glabrous. Color: When opening, upper surface: Close to 43A. When opening, lower surface: Close to 43A marbled with close to 33A. Fully opened, upper surface: Close to 43A marbled with close to 33A; after anthesis, color becomes closer to 53B. Fully opened, lower surface: Close to 33B shifting to closer to 17B; after anthesis, color becomes closer to 53B.

*Sepals*.—Quantity and arrangement: Two, opposite. Length: About 1 cm. Width: About 7 mm. Shape: Deltoid. Apex: Acute. Base: Truncate. Margin: Entire. Texture, upper surface: Smooth, glabrous. Texture, lower surface: Smooth, glabrous; leathery. Color, upper and lower surfaces: Close to 147C.

*Peduncles*.—Length: About 2 mm. Diameter: About 2 mm. Angle: Mostly upright. Strength: Strong. Texture: Smooth, glabrous; succulent. Color: Close to 146C.

*Reproductive organs*.—None observed as all reproductive organs are transformed into petaloids.

*Seeds & fruits*.—Seed and fruit production have not been observed on plants of the new *Portulaca*.

Garden performance: Plants of the new *Portulaca* have been observed to have excellent garden performance and to tolerate rain, wind, drought, heat and low temperatures about 10° C.

Pathogen & pest resistance: Plants of the new *Portulaca* have been observed to be resistant to *Phytophthora*. Plants of the new *Portulaca* have not been shown to be resistant to pests and other pathogens common to *Portulaca* plants.

It is claimed:

1. A new and distinct *Portulaca* plant named 'LAZPRT1507' as illustrated and described.

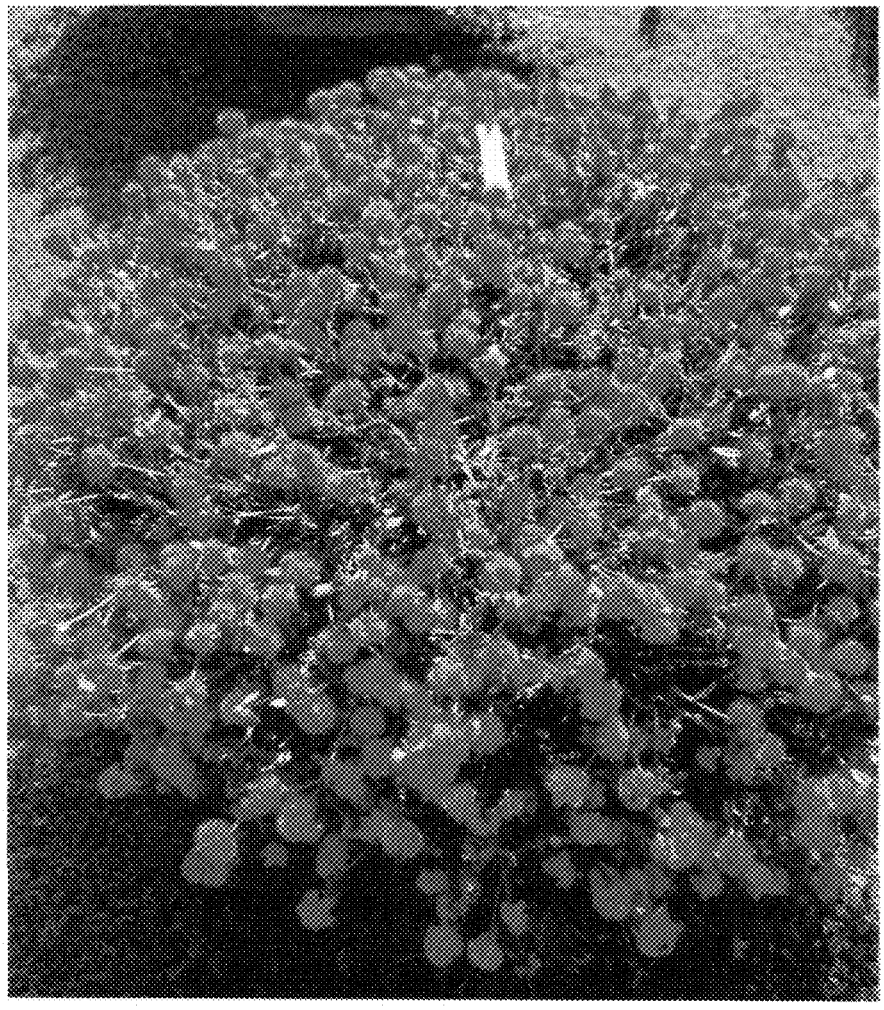

* * * * *